US012465358B2

(12) United States Patent
Jin et al.

(10) Patent No.: US 12,465,358 B2
(45) Date of Patent: Nov. 11, 2025

(54) END EFFECTOR FOR SURGICAL STAPLING DEVICE

(71) Applicant: Covidien LP, Mansfield, MA (US)

(72) Inventors: Tingting Jin, Shanghai (CN); Syed Sarfraz Ahamed, Shanghai (CN); Xiliang Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 78 days.

(21) Appl. No.: 18/558,762

(22) PCT Filed: May 7, 2021

(86) PCT No.: PCT/CN2021/091986

§ 371 (c)(1),
(2) Date: Nov. 3, 2023

(87) PCT Pub. No.: WO2022/233014

PCT Pub. Date: Nov. 10, 2022

(65) Prior Publication Data

US 2025/0072892 A1 Mar. 6, 2025

(51) Int. Cl.
*A61B 17/072* (2006.01)
*A61B 17/00* (2006.01)

(52) U.S. Cl.
CPC .. *A61B 17/072* (2013.01); *A61B 2017/00477* (2013.01); *A61B 2017/07257* (2013.01)

(58) Field of Classification Search
CPC ........ A61B 17/072; A61B 2017/00477; A61B 2017/07257
See application file for complete search history.

(56) References Cited

U.S. PATENT DOCUMENTS 1,158,111 A 10/1915 Ahlheim
2,891,250 A 6/1959 Hirata
3,080,564 A 3/1963 Strekopitov et al.
3,252,643 A 5/1966 Strekopov et al.
3,269,630 A 8/1966 Fleischer
3,275,211 A 9/1966 Hirsch et al.
3,315,863 A 4/1967 O'Dea
3,494,533 A 2/1970 Green et al.
(Continued)

FOREIGN PATENT DOCUMENTS

CN 108472040 B 6/2021
CN 108472036 B 7/2021
(Continued)

OTHER PUBLICATIONS

International Search Report for Application No. PCT/CN2021/091986 dated Jun. 30, 2021.
(Continued)

*Primary Examiner* — Robert F Long
*Assistant Examiner* — Eduardo R Ferrero

(57) ABSTRACT

A surgical stapling device includes an end effector having an end effector frame with a cantilevered portion and an anvil assembly supported on the cantilevered portion of the end effector frame. The anvil assembly and the cantilevered portion of the end effector frame are adapted to be secured together in a manner to minimize weakening of the cantilevered portion of the end effector frame to minimize deflection of the anvil assembly during firing of the stapling device.

11 Claims, 9 Drawing Sheets

(56) References Cited

U.S. PATENT DOCUMENTS

| | | | | | |
|---|---|---|---|---|---|
| 3,589,589 | A | | 6/1971 | Akopov | |
| 3,692,224 | A | | 9/1972 | Astafiev et al. | |
| 3,795,034 | A | | 3/1974 | Strekopytov et al. | |
| 3,822,818 | A | | 7/1974 | Strekopytov et al. | |
| 3,935,981 | A | | 2/1976 | Akopov et al. | |
| 3,949,923 | A | | 4/1976 | Akopov et al. | |
| 4,047,654 | A | | 9/1977 | Alvarado | |
| 4,216,891 | A | | 8/1980 | Behlke | |
| 4,244,372 | A | | 1/1981 | Kapitanov et al. | |
| 4,296,881 | A | | 10/1981 | Lee | |
| 4,305,539 | A | | 12/1981 | Korolkov et al. | |
| 4,354,628 | A | | 10/1982 | Green | |
| 4,378,901 | A | | 4/1983 | Akopov et al. | |
| 4,383,634 | A | | 5/1983 | Green | |
| 4,402,444 | A | | 9/1983 | Green | |
| 4,415,112 | A | | 11/1983 | Green | |
| D273,513 | S | | 4/1984 | Spreckelmeier | |
| 4,442,964 | A | | 4/1984 | Becht | |
| 4,470,533 | A | | 9/1984 | Schuler | |
| 4,475,679 | A | | 10/1984 | Fleury, Jr. | |
| 4,485,811 | A | | 12/1984 | Chernousov et al. | |
| 4,506,670 | A | | 3/1985 | Crossley | |
| 4,506,671 | A | | 3/1985 | Green | |
| 4,508,253 | A | | 4/1985 | Green | |
| 4,522,327 | A | | 6/1985 | Korthoff et al. | |
| 4,527,724 | A | | 7/1985 | Chow et al. | |
| 4,530,453 | A | | 7/1985 | Green | |
| 4,550,870 | A | | 11/1985 | Krumme et al. | |
| 4,566,620 | A | | 1/1986 | Green et al. | |
| 4,568,009 | A | | 2/1986 | Green | |
| 4,573,622 | A | | 3/1986 | Green et al. | |
| 4,580,712 | A | | 4/1986 | Green | |
| 4,585,153 | A | | 4/1986 | Failla et al. | |
| 4,589,582 | A | | 5/1986 | Bilotti | |
| 4,602,634 | A | | 7/1986 | Barkley | |
| 4,605,001 | A | | 8/1986 | Rothfuss et al. | |
| 4,605,004 | A | | 8/1986 | Di Giovanni et al. | |
| 4,606,344 | A | | 8/1986 | Di Giovanni | |
| 4,606,345 | A | | 8/1986 | Dorband et al. | |
| 4,607,636 | A | | 8/1986 | Kula et al. | |
| 4,612,933 | A | | 9/1986 | Brinkerhoff et al. | |
| 4,617,928 | A | | 10/1986 | Alfranca | |
| 4,632,290 | A | | 12/1986 | Green et al. | |
| 4,665,916 | A | * | 5/1987 | Green .................. | A61B 17/072 227/19 |
| 4,684,051 | A | | 8/1987 | Akopov et al. | |
| 4,714,187 | A | * | 12/1987 | Green .................. | A61B 17/072 227/19 |
| 4,715,520 | A | * | 12/1987 | Roehr, Jr. ............ | A61B 17/072 227/19 |
| 4,728,020 | A | | 3/1988 | Green et al. | |
| 4,767,044 | A | | 8/1988 | Green | |
| 4,788,978 | A | | 12/1988 | Strekopytov et al. | |
| 4,802,614 | A | | 2/1989 | Green et al. | |
| 4,805,823 | A | | 2/1989 | Rothfuss | |
| 4,819,853 | A | | 4/1989 | Green | |
| 4,848,637 | A | | 7/1989 | Pruitt | |
| 4,869,414 | A | | 9/1989 | Green et al. | |
| 4,881,544 | A | | 11/1989 | Green et al. | |
| 4,881,545 | A | | 11/1989 | Isaacs et al. | |
| 4,915,100 | A | | 4/1990 | Green | |
| 4,930,503 | A | | 6/1990 | Pruitt | |
| 4,938,408 | A | | 7/1990 | Bedi et al. | |
| 4,941,623 | A | | 7/1990 | Pruitt | |
| 4,951,861 | A | | 8/1990 | Schulze et al. | |
| 4,964,559 | A | | 10/1990 | Deniega et al. | |
| 5,005,754 | A | | 4/1991 | Van Overloop | |
| 5,018,657 | A | | 5/1991 | Pedlick et al. | |
| 5,071,052 | A | | 12/1991 | Rodak et al. | |
| 5,100,042 | A | | 3/1992 | Gravener et al. | |
| 5,116,349 | A | | 5/1992 | Aranyi | |
| 5,137,198 | A | | 8/1992 | Nobis et al. | |
| 5,172,845 | A | | 12/1992 | Tejeiro | |
| 5,190,203 | A | | 3/1993 | Rodak | |
| 5,219,111 | A | | 6/1993 | Bilotti et al. | |
| 5,240,163 | A | | 8/1993 | Stein et al. | |
| 5,344,060 | A | | 9/1994 | Gravener et al. | |
| 5,368,599 | A | | 11/1994 | Hirsch et al. | |
| 5,405,073 | A | | 4/1995 | Porter | |
| 5,413,267 | A | | 5/1995 | Solyntjes et al. | |
| 5,439,155 | A | | 8/1995 | Viola | |
| 5,452,836 | A | * | 9/1995 | Huitema .............. | A61B 17/072 227/176.1 |
| 5,458,279 | A | * | 10/1995 | Plyley .................. | A61B 17/072 227/176.1 |
| 5,462,215 | A | | 10/1995 | Viola et al. | |
| 5,464,144 | A | | 11/1995 | Guy et al. | |
| 5,465,894 | A | | 11/1995 | Clark et al. | |
| 5,470,006 | A | | 11/1995 | Rodak | |
| 5,470,008 | A | | 11/1995 | Rodak | |
| 5,470,009 | A | | 11/1995 | Rodak | |
| 5,497,934 | A | | 3/1996 | Brady et al. | |
| 5,503,320 | A | | 4/1996 | Webster et al. | |
| 5,509,596 | A | | 4/1996 | Green et al. | |
| 5,542,594 | A | | 8/1996 | McKean et al. | |
| 5,547,117 | A | | 8/1996 | Hamblin et al. | |
| 5,558,266 | A | | 9/1996 | Green et al. | |
| 5,571,285 | A | | 11/1996 | Chow et al. | |
| 5,579,978 | A | | 12/1996 | Green et al. | |
| 5,580,067 | A | | 12/1996 | Hamblin et al. | |
| 5,603,443 | A | | 2/1997 | Clark et al. | |
| 5,605,272 | A | | 2/1997 | Witt et al. | |
| 5,605,273 | A | | 2/1997 | Hamblin et al. | |
| 5,607,094 | A | | 3/1997 | Clark et al. | |
| 5,615,820 | A | | 4/1997 | Viola | |
| 5,636,779 | A | * | 6/1997 | Palmer ................. | A61B 17/072 227/176.1 |
| 5,641,111 | A | | 6/1997 | Ahrens et al. | |
| 5,678,748 | A | | 10/1997 | Plyley et al. | |
| 5,697,543 | A | | 12/1997 | Burdorff | |
| 5,706,997 | A | | 1/1998 | Green et al. | |
| 5,706,998 | A | | 1/1998 | Plyley et al. | |
| 5,732,871 | A | | 3/1998 | Clark et al. | |
| 5,735,445 | A | | 4/1998 | Vidal et al. | |
| 5,794,834 | A | | 8/1998 | Hamblin et al. | |
| 5,810,240 | A | | 9/1998 | Robertson | |
| 5,855,311 | A | | 1/1999 | Hamblin et al. | |
| 5,878,937 | A | | 3/1999 | Green et al. | |
| 5,893,506 | A | | 4/1999 | Powell | |
| 5,894,979 | A | | 4/1999 | Powell | |
| 5,964,394 | A | | 10/1999 | Robertson | |
| 6,045,560 | A | | 4/2000 | McKean et al. | |
| 6,638,285 | B2 | | 10/2003 | Gabbay | |
| 6,805,273 | B2 | | 10/2004 | Bilotti et al. | |
| 6,817,508 | B1 | | 11/2004 | Racenet et al. | |
| 6,988,650 | B2 | | 1/2006 | Schwemberger et al. | |
| 7,070,083 | B2 | | 7/2006 | Jankowski | |
| 7,134,587 | B2 | | 11/2006 | Schwemberger et al. | |
| 7,147,139 | B2 | | 12/2006 | Schwemberger et al. | |
| 7,147,140 | B2 | | 12/2006 | Wukusick et al. | |
| 7,204,404 | B2 | | 4/2007 | Nguyen et al. | |
| 7,207,472 | B2 | | 4/2007 | Wukusick et al. | |
| 7,210,609 | B2 | | 5/2007 | Leiboff et al. | |
| 7,237,708 | B1 | | 7/2007 | Guy et al. | |
| 7,275,674 | B2 | | 10/2007 | Racenet et al. | |
| RE40,237 | E | | 4/2008 | Bilotti et al. | |
| 7,407,076 | B2 | | 8/2008 | Racenet et al. | |
| 7,431,190 | B2 | | 10/2008 | Hoffman | |
| 7,522,854 | B2 | | 4/2009 | Kinouchi et al. | |
| 7,549,563 | B2 | | 6/2009 | Mather et al. | |
| 7,568,605 | B2 | | 8/2009 | Kruszynski | |
| 7,641,092 | B2 | | 1/2010 | Kruszynski et al. | |
| 7,717,312 | B2 | | 5/2010 | Beetel | |
| 7,731,073 | B2 | | 6/2010 | Wixey et al. | |
| 7,735,704 | B2 | | 6/2010 | Bilotti | |
| 7,766,207 | B2 | | 8/2010 | Mather et al. | |
| 7,810,690 | B2 | | 10/2010 | Bilotti et al. | |
| 7,828,188 | B2 | | 11/2010 | Jankowski | |
| 7,886,953 | B2 | | 2/2011 | Schwemberger et al. | |
| 8,016,176 | B2 | | 9/2011 | Kasvikis et al. | |
| 8,029,520 | B2 | | 10/2011 | Korvick et al. | |
| 8,033,439 | B2 | | 10/2011 | Racenet et al. | |
| 8,070,038 | B2 | | 12/2011 | Kostrzewski | |
| 8,231,041 | B2 | | 7/2012 | Marczyk et al. | |

(56) References Cited

U.S. PATENT DOCUMENTS 8,292,904 B2 10/2012 Popovic et al.
8,328,064 B2 12/2012 Racenet et al.
8,360,296 B2 1/2013 Zingman
8,424,738 B2 4/2013 Kasvikis
8,479,969 B2 * 7/2013 Shelton, IV ..... A61B 17/00234 227/19
8,499,994 B2 8/2013 D'Arcangelo
8,573,465 B2 * 11/2013 Shelton, IV ........... A61B 17/32 227/19
8,596,515 B2 12/2013 Okoniewski
8,627,994 B2 1/2014 Zemlok et al.
8,646,673 B2 2/2014 Bilotti et al.
8,757,467 B2 6/2014 Racenet et al.
8,800,838 B2 * 8/2014 Shelton, IV ..... A61B 17/07207 227/176.1
8,936,185 B2 1/2015 Racenet et al.
8,955,732 B2 2/2015 Zemlok et al.
8,967,446 B2 3/2015 Beardsley et al.
9,022,273 B1 5/2015 Marczyk et al.
9,125,651 B2 9/2015 Mandakolathur Vasudevan et al.
9,192,382 B2 11/2015 Kostrzewski
9,192,387 B1 11/2015 Holsten et al.
9,480,474 B2 11/2016 Ji et al.
9,566,066 B2 2/2017 Kasvikis
9,579,102 B2 2/2017 Holsten et al.
9,655,619 B2 5/2017 Zhang et al.
9,662,111 B2 5/2017 Holsten et al.
9,668,736 B2 6/2017 Holsten et al.
9,675,349 B2 6/2017 Holsten et al.
9,675,350 B2 6/2017 Holsten et al.
9,675,356 B2 6/2017 Racenet et al.
9,814,460 B2 11/2017 Kimsey et al.
9,888,923 B2 2/2018 Chen et al.
9,962,159 B2 5/2018 Heinrich et al.
10,004,504 B2 6/2018 Bryant
10,085,754 B2 10/2018 Sniffin et al.
10,194,913 B2 * 2/2019 Nalagatla ........... A61B 17/1155
2004/0164123 A1 8/2004 Racenet et al.
2005/0139636 A1 * 6/2005 Schwemberger .... A61B 17/072 227/19
2005/0143759 A1 * 6/2005 Kelly ................... A61B 17/072 606/139
2005/0145672 A1 * 7/2005 Schwemberger .... A61B 17/072 227/176.1
2005/0247752 A1 11/2005 Kelly et al.
2005/0247753 A1 11/2005 Kelly et al.
2006/0163312 A1 7/2006 Viola et al.
2007/0187456 A1 8/2007 Viola et al.
2008/0083812 A1 * 4/2008 Scirica ................. A61B 17/068 227/176.1
2009/0134199 A1 * 5/2009 Heinrich .......... A61B 17/07207 606/49
2010/0048988 A1 2/2010 Pastorelli et al.
2013/0206813 A1 8/2013 Nalagatla
2014/0110457 A1 * 4/2014 Zhang ................ A61B 17/1155 227/177.1
2015/0119904 A1 * 4/2015 Ji ..................... A61B 17/06166 606/144
2016/0249914 A1 9/2016 Zhang et al.
2016/0249923 A1 9/2016 Hodgkinson et al.
2016/0270784 A1 9/2016 Wheeler et al.
2016/0270790 A1 9/2016 Jankowski
2016/0270793 A1 9/2016 Carter et al.
2016/0278779 A1 9/2016 Jankowski
2017/0014134 A1 1/2017 Chen et al.
2017/0027571 A1 2/2017 Nalagatla et al.
2017/0027572 A1 2/2017 Nalagatla et al.
2017/0027573 A1 2/2017 Nalagatla et al.
2017/0027574 A1 2/2017 Nalagatla et al.
2017/0128149 A1 5/2017 Heinrich et al.
2017/0189012 A1 * 7/2017 Adams ................. A61B 17/072
2017/0189022 A1 * 7/2017 Adams ................. A61B 17/072
2017/0238923 A1 8/2017 Holsten et al.
2017/0238924 A1 8/2017 Holsten et al.
2017/0265861 A1 9/2017 Holsten et al.
2018/0008261 A1 1/2018 Racenet et al.
2018/0049739 A1 2/2018 Kasvikis
2018/0153544 A1 6/2018 Maddur Shankarsetty et al.
2018/0221024 A1 8/2018 Heinrich et al.
2019/0298356 A1 * 10/2019 Shelton, IV ..... A61B 17/07207
2019/0314019 A1 * 10/2019 Rector ............ A61B 17/07207
2020/0337698 A1 10/2020 Simms
2020/0337701 A1 * 10/2020 Campbell ........ A61B 17/07207
2021/0186498 A1 * 6/2021 Boudreaux ...... A61B 17/07207
2022/0249090 A1 * 8/2022 Zhang .................. A61B 17/072
2023/0007859 A1 * 1/2023 Adams ................. A61B 17/072
2023/0047701 A1 * 2/2023 Zhang .................. A61B 17/072
2023/0157688 A1 * 5/2023 Guo ..................... A61B 17/072 227/180.1
2024/0090897 A1 * 3/2024 Zhang .................. A61B 17/072
2024/0138833 A1 * 5/2024 Wang ................... A61B 17/072
2025/0072892 A1 * 3/2025 Jin ....................... A61B 17/072

FOREIGN PATENT DOCUMENTS

CN 111466975 B 4/2022
WO WO-2014043971 A1 * 3/2014 ........... A61B 17/072

OTHER PUBLICATIONS

Written Opinion for Application No. PCT/CN2021/091986 dated Jun. 30, 2021.

* cited by examiner

END EFFECTOR FOR SURGICAL STAPLING DEVICE

FIELD

This technology is generally related to surgical stapling devices and, more particularly, to surgical stapling devices with cantilevered anvil assemblies.

BACKGROUND

Surgical stapling devices are commonly used during a variety of surgical procedures to expedite dissection and suturing of tissue and minimize trauma to a patient. Typically, these stapling devices include an end effector that includes a cartridge assembly and an anvil assembly that are movable in relation to each other between open and clamped positions. Some stapling devices include an end effector frame that has first and second transverse portions that are joined together by a longitudinal portion. The cartridge assembly is supported on a clamp slide assembly that is positioned adjacent the first transverse portion and the anvil assembly is supported on the second transverse portion. The second transverse portion is supported on the longitudinal portion in cantilevered fashion. When the stapling device is fired, the second transverse portion may deflect and cause the anvil assembly to become slightly misaligned with the cartridge assembly. This may result in staple malformation.

Typically, the anvil assembly is secured to the second transverse portion of the end effector frame using rivets that are received in through holes in the second transverse portion. The through holes weaken the second transverse portion which leads to more deflection of the second transverse portion when the stapling device is fired. When rivets are used to secure the anvil assembly to the second transverse portion of the end effector frame, the riveting tolerances may result in misalignment of the anvil assembly with the cartridge assembly also resulting in staple malformation. Since the rivets fixedly secure the anvil assembly to the end effector frame, any misalignment that may result cannot be corrected.

A continuing need exists in the art for a surgical stapling device including an anvil assembly that is secured to the end effector frame in a manner that does not weaken the end effector frame.

SUMMARY

This disclosure is directed to a surgical stapling device that includes an end effector having an end effector frame with a cantilevered portion and an anvil assembly supported on the cantilevered portion of the end effector frame. The anvil assembly and the cantilevered portion of the end effector frame are adapted to be secured together in a manner to minimize weakening of the cantilevered portion of the end effector frame to minimize deflection of the anvil assembly during firing of the stapling device.

Aspects of this disclosure are directed to an end effector for a surgical device that includes an end effector frame and an anvil assembly. The end effector frame includes a distal transverse portion, a proximal transverse portion, and a longitudinal portion. The longitudinal portion interconnects the distal transverse portion and the proximal transverse portion at spaced positions to define a gap between the distal and proximal transverse portions. The distal transverse portion includes a proximally facing surface. The anvil assembly includes a cut plate and an anvil. The anvil assembly is secured to the distal transverse portion of the end effector frame via a snap-fit connection such that the cut plate is sandwiched between the anvil and the proximally facing surface of the distal transverse portion.

In aspects of the disclosure, the cut plate includes a base wall and a side wall positioned about the base wall to define proximal and distal recesses.

In some aspects of the disclosure, the anvil is received within the proximal recess of the cut plate and the proximally facing surface of the distal transverse portion of the end effector frame is received within the distal recess of the cut plate.

In certain aspects of the disclosure, the anvil defines a knife slot, and the cut plate includes a rib that extends into the knife slot.

In aspects of the disclosure, the anvil includes a staple forming surface and brackets positioned about and extending distally from the staple forming surface.

In some aspects of the disclosure, the brackets are engaged with the distal transverse portion of the end effector frame to secure the anvil to the end effector frame.

In certain aspects of the disclosure, each of the brackets includes a resilient finger and the distal transverse portion of the end effector frame defines openings that receive the resilient fingers in snap-fit fashion to secure the anvil to the distal transverse portion of the end effector frame.

In aspects of the disclosure, each of the brackets defines an opening and the distal transverse portion of the end effector frame includes a side wall that has protrusions.

In some aspects of the disclosure, the protrusions are received within the openings of the brackets in snap-fit fashion to secure the anvil to the distal transverse portion of the end effector frame.

In certain aspects of the disclosure, the distal transverse portion of the end effector frame defines a recess that is positioned about the proximally facing surface of the anvil, and the side wall of the cut plate is received at least partially within the recess.

In aspects of the disclosure, the base wall of the cut plate defines through bores that receive the brackets of the anvil.

In some aspects of the disclosure, the side wall of the distal transverse portion of the end effector frame defines slots and the side wall of the cut plate includes tabs that are received within the slots and cover the snap-fit connection.

Other aspects of the disclosure are directed to a surgical stapling device including an elongate frame, a clamp slide assembly, and an end effector. The elongate frame has a proximal portion and a distal portion and defines a channel. The clamp slide assembly is positioned within the channel and has a distal portion defining a cavity. The end effector includes an end effector frame, a cartridge assembly, and an anvil assembly. The end effector frame has a distal transverse portion, a proximal transverse portion, and a longitudinal portion. The longitudinal portion interconnects the distal transverse portion and the proximal transverse portion at spaced positions to define a gap between the distal and proximal transverse portions. The distal transverse portion includes a proximally facing surface, and the distal portion of the clamp slide assembly is received within the gap. The cartridge assembly is supported on the distal portion of the clamp slide assembly within the gap. The anvil assembly includes a cut plate and an anvil. The anvil assembly is secured to the distal transverse portion of the end effector frame via a snap-fit connection such that the cut plate is sandwiched between the anvil and the proximally facing surface of the distal transverse portion.

Still other aspects of the disclosure are directed to an end effector including an end effector frame, a cartridge assembly, and an anvil assembly. The end effector frame includes a first transverse portion, a second transverse portion, and a longitudinal portion. The longitudinal portion interconnects the first transverse portion and the second transverse portion at spaced positions to define a gap between the first and second transverse portions. The first transverse portion includes a proximally facing surface. The cartridge assembly is supported within the gap of the end effector frame and is movable between an unclamped position spaced from the first transverse portion and a clamped position adjacent the first transverse portion. The anvil assembly includes a cut plate and an anvil. The anvil assembly is secured to the first transverse portion of the end effector frame via a snap-fit connection such that the cut plate is sandwiched between the anvil and the proximally facing surface of the first transverse portion.

Other features of the disclosure will be appreciated from the following description.

BRIEF DESCRIPTION OF THE DRAWINGS

Various aspects of the disclosure are described herein below with reference to the drawings, wherein.

DETAILED DESCRIPTION

Figure 1:
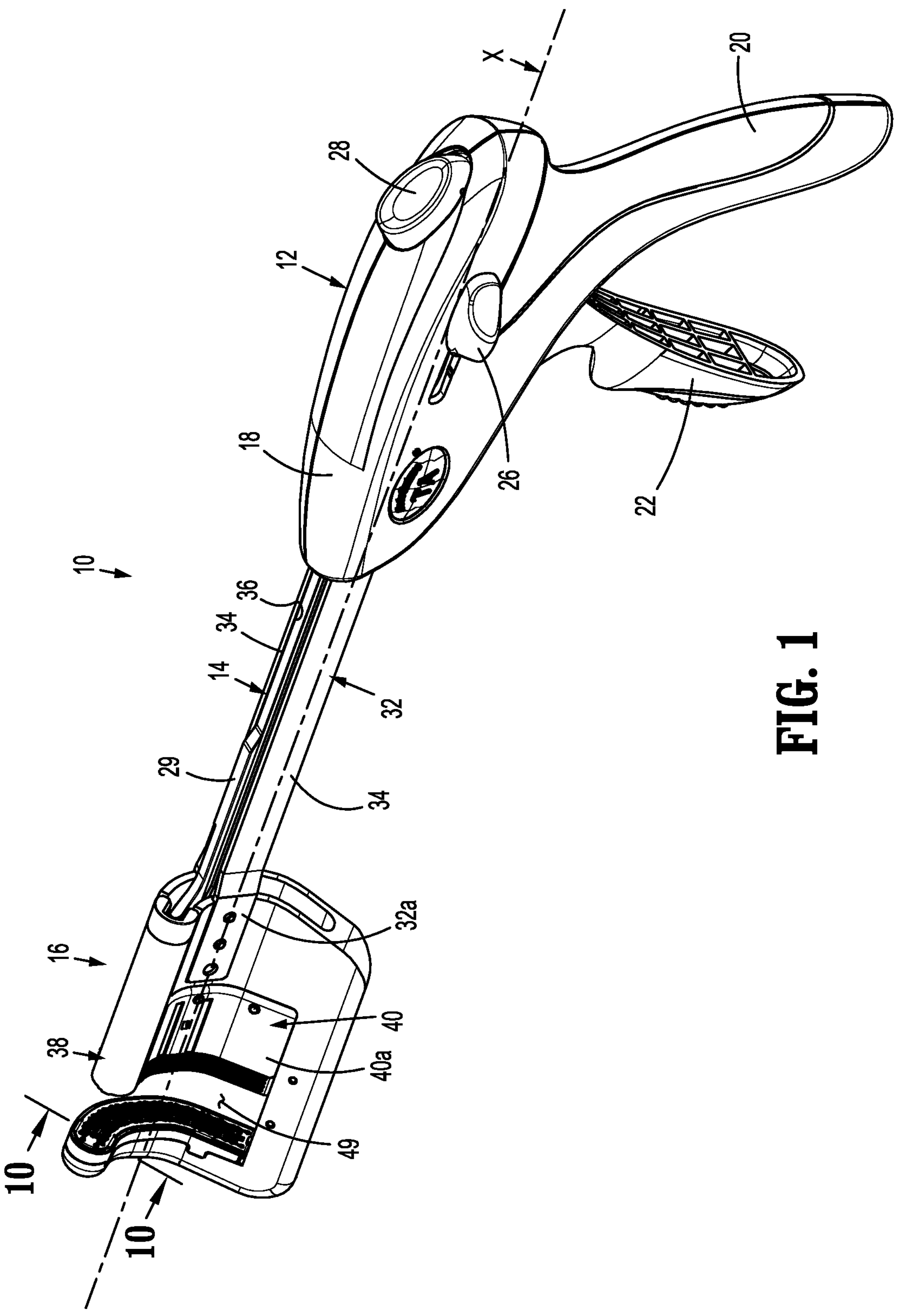
FIG. 1 is a side perspective view of a surgical stapling device according to aspects of the disclosure in an open or unclamped pre-fired position.
Figure 2:
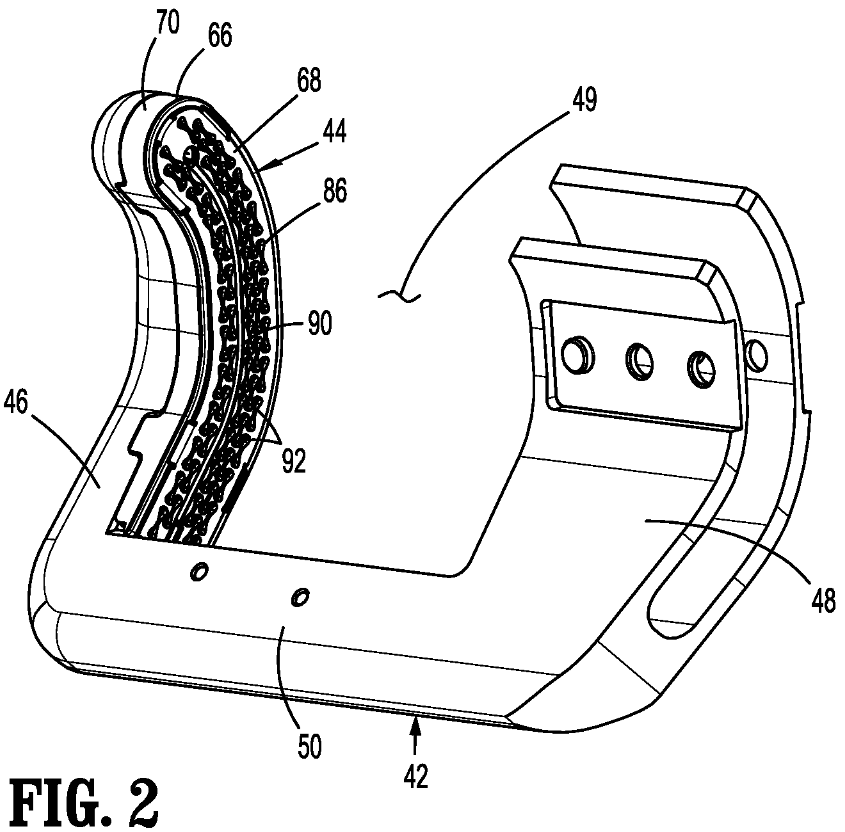
FIG. 2 is a side perspective view of an end effector frame and anvil assembly of the stapling device shown in FIG. 1 from a first side of the end effector frame with the anvil assembly secured to the end effector frame.
Figure 3:
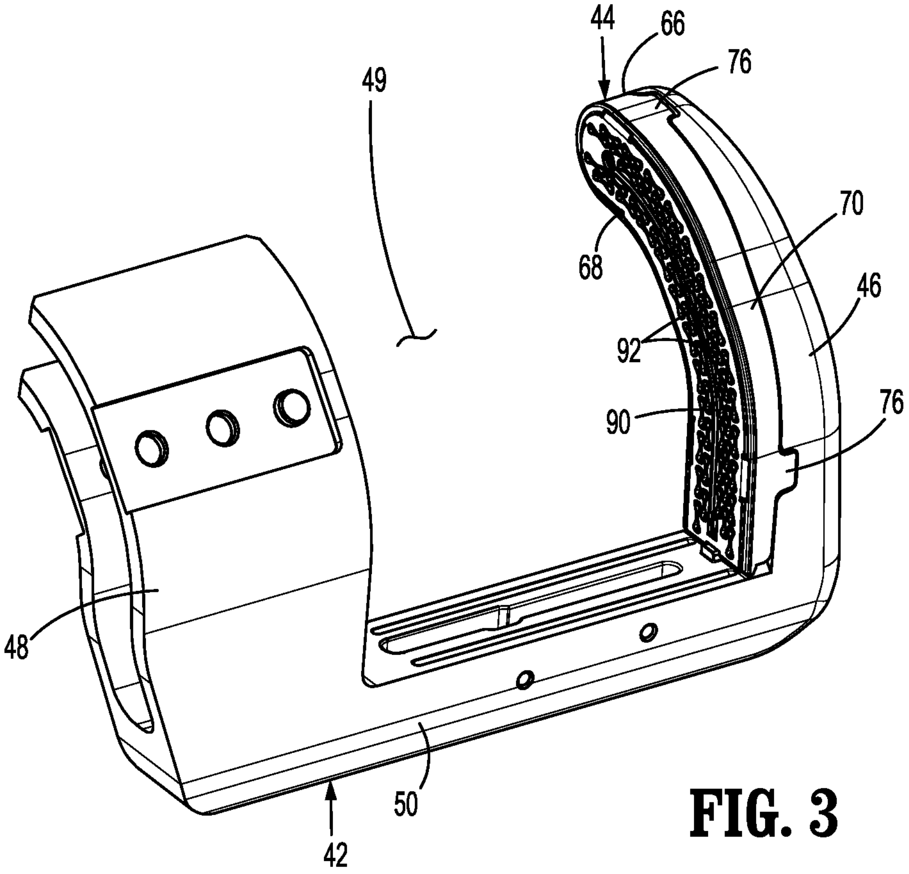
FIG. 3 is a side perspective view of the end effector frame and anvil assembly shown in FIG. 2 from a second side of the end effector frame with the anvil assembly secured to the end effector frame.
Figure 4:
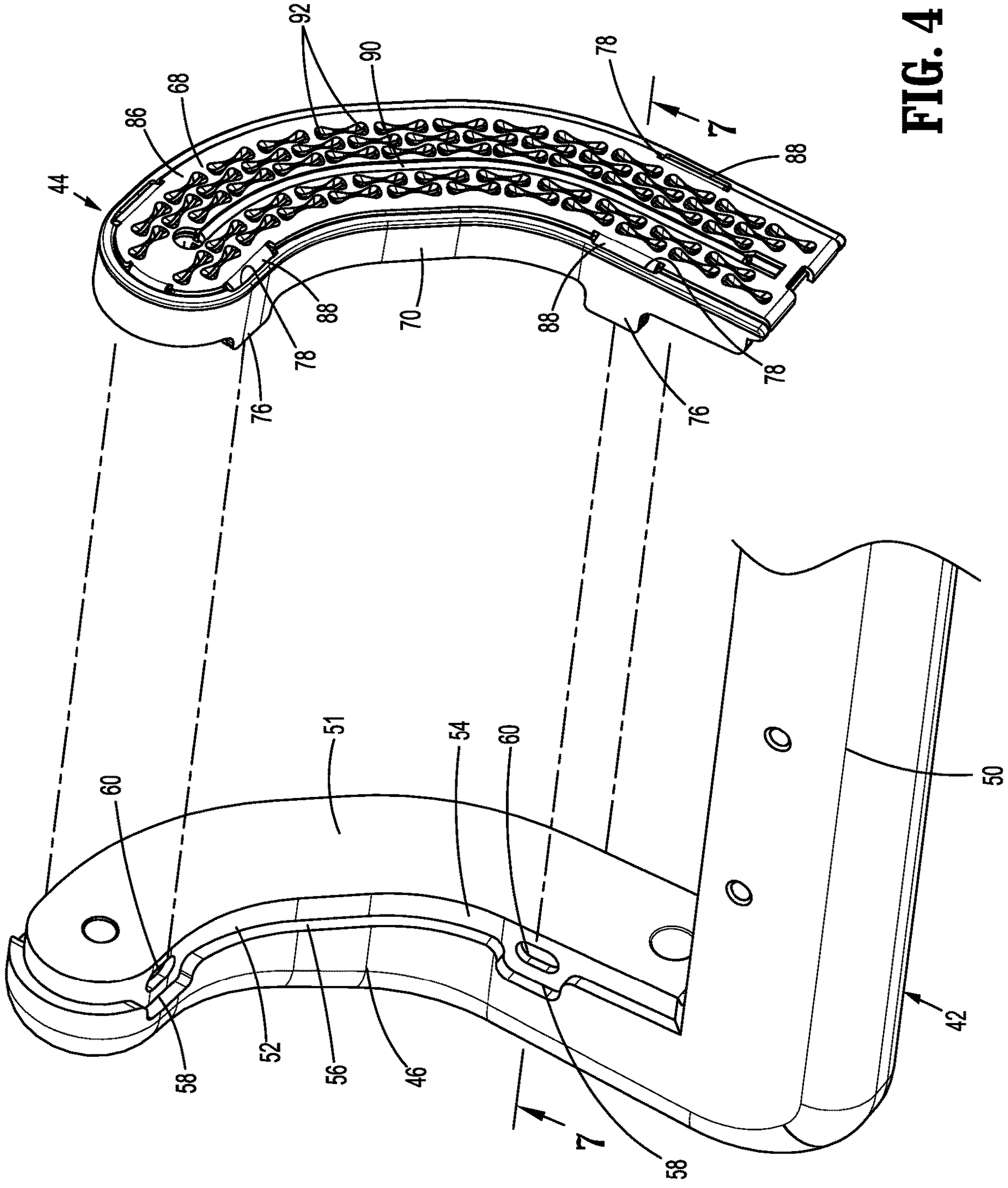
FIG. 4 is a side perspective view from the distal end of an anvil of the anvil assembly shown in FIG. 3.
Figure 6:
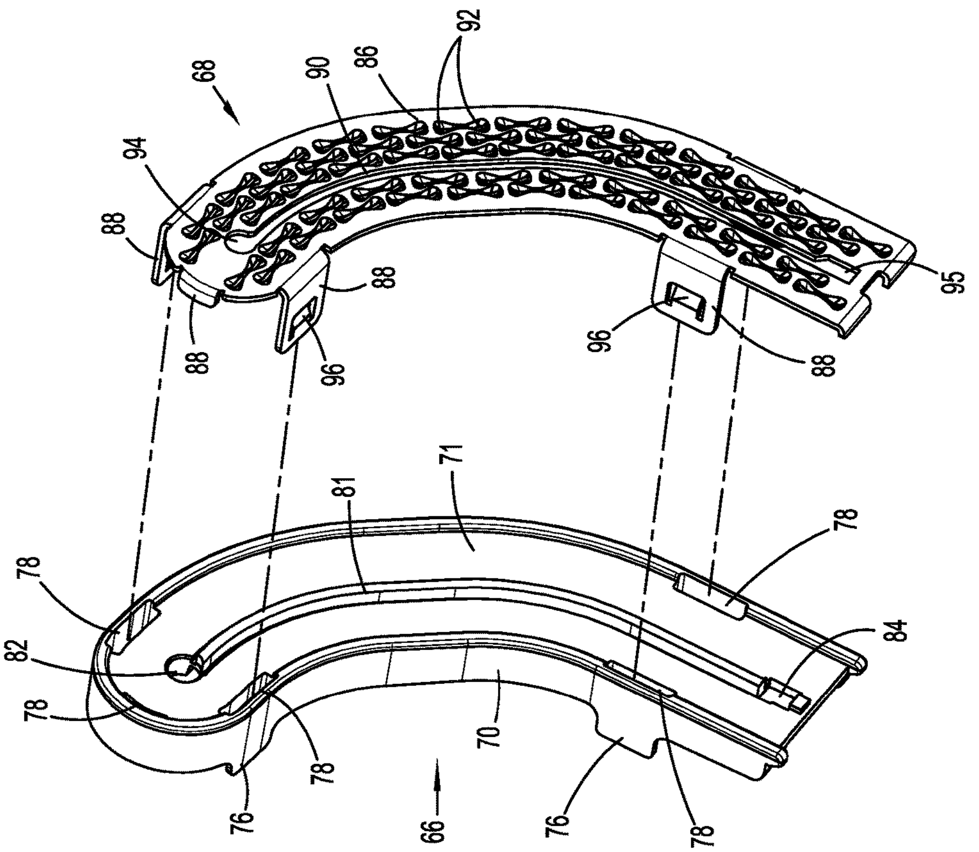
FIG. 6 is a side perspective view of a distal portion of the end effector frame and the anvil assembly shown in 2 with the anvil assembly separated from the end effector frame.
Figure 5:
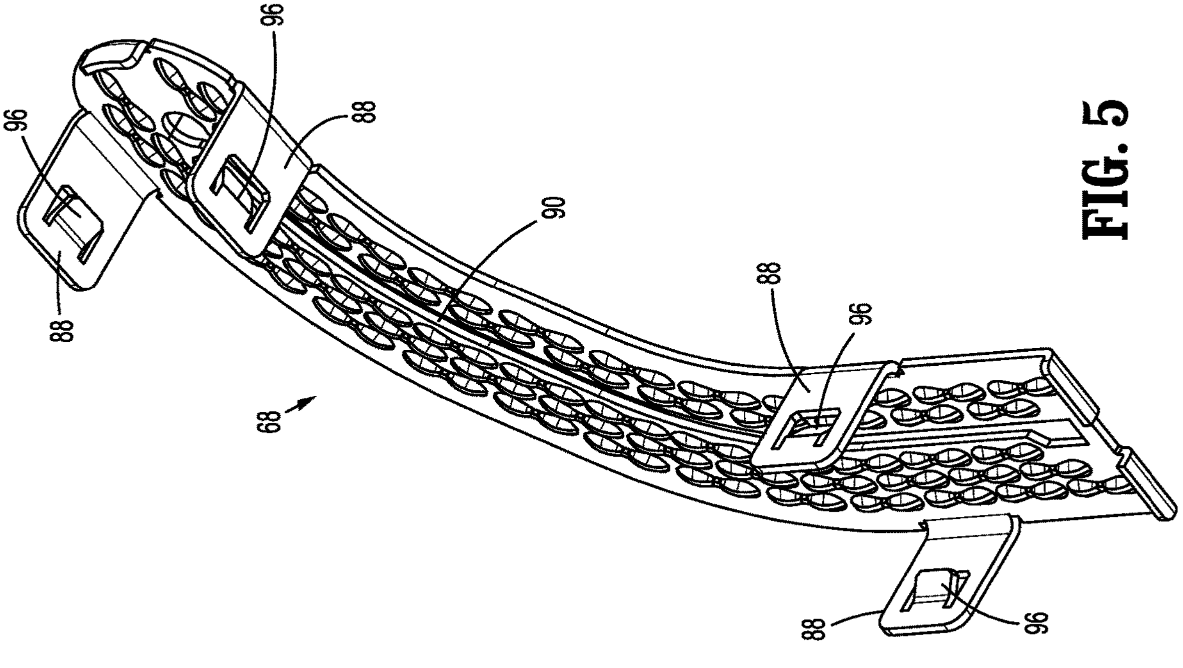
FIG. 5 is a side perspective view from the proximal end of the anvil assembly shown in FIG. 3 with the anvil separated from a cut plate of the anvil assembly.

The disclosed surgical stapling device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the stapling device in its customary manner, while the term "distal" is used generally to refer to that portion of the device that is farther from the clinician during use of the stapling device in its customary manner. In addition, the term "clinician" is used generally to refer to medical personnel including doctors, nurses, and support personnel. Further, directional terms such as front, rear, upper, lower, top, bottom, and similar terms are used to assist in understanding the description and are not intended to limit the disclosure.

This disclosure is directed to a surgical stapling device that includes an end effector including an end effector frame and an anvil assembly that is secured to the end effector frame in a manner to prevent weakening of the end effector frame and minimize deflection of the anvil assembly during firing of the stapling device.

FIG. 1 illustrates a surgical stapling device according to aspects of the disclosure shown generally as stapling device 10. The stapling device 10 includes a handle assembly 12, an elongate body 14 that extends distally from the handle assembly 12, and an end effector 16 that is supported on a distal portion of the elongate body 14. The elongate body 14 defines a longitudinal axis "X". The handle assembly 12 includes a housing 18 that defines a stationary handle 20 and supports a movable trigger 22. In aspects of the disclosure, the trigger 22 is supported by the housing 18 to pivot towards the stationary handle 20 between non-actuated and actuated positions to actuate the end effector 16, i.e., move the end effector 16 between open and clamped positions and fire the stapling device 10. The handle assembly 12 also supports two buttons 26 (only one is shown), one being positioned on each side of the housing 18, that are movable along the housing 18 to advance and retract an alignment pin pusher 30. The handle assembly 12 also includes a release button 28 that can be depressed to move the end effector 16 from the clamped position to the open position. For a more detailed description of a representative handle assembly 12, see, e.g., U.S. Pat. No. 6,817,508 ("the '508 Patent").

The stapling device 10 includes a frame 32 that extends from the handle assembly 12 and includes a distal portion **32*a* that supports the end effector 16. The frame 32 includes spaced frame members 34 that define a channel 36 that receives a thrust bar (not shown) and the alignment pin pusher 30. The thrust bar (not shown) is movable within the channel 36 between retracted and advanced positions in response to movement of the trigger 22 to actuate the stapling device 10. The channel 36 defined by the frame members 34 also receive a clamp slide assembly 40 that extends into the end effector 16 and supports a cartridge assembly 38. In aspects of the disclosure, the cartridge assembly 38 is releasably coupled to the clamp slide assembly 40. For a more detailed description of the interaction between the trigger 22, the thrust bar, and the clamp slide assembly 40**, see the '508 Patent.

FIGS. 2-6 illustrate portions of the end effector 16 including an end effector frame 42 and an anvil assembly 44. The end effector frame 42 is secured to the distal portion 32*a* (FIG. 1) of the frame 32 of the stapling device 10 (FIG. 1) and includes a distal transverse portion 46, a proximal transverse portion 48, and a longitudinal portion 50 that interconnects the distal transverse portion 46 and the proximal transverse portion 48. The distal and proximal transverse portions 46, 48 are spaced from each other to define a gap 49 between the distal and proximal transverse portions 46, 48. In some aspects of the disclosure, the distal and proximal transverse portions 46, 48 are curved along axes transverse to the longitudinal axis "X" of the elongate body 14 of the stapling device 10 (FIG. 1). In some aspects of the disclosure, the distal and proximal transverse portions 46, 48 are formed from a plurality of linear portions, e.g., three, that are positioned at angles in relation to each other.

The clamp slide assembly 40 includes a proximal portion (not shown) that is coupled to the handle assembly 12 and a distal portion 40*a* (FIG. 1) that is received within the gap 49 defined between the distal and proximal transverse portions 46, 48 of the end effector frame 42. The distal portion 40*a* (FIG. 1) of the clamp slide assembly 40 defines a cavity (not shown) that receives the cartridge assembly 38. A distal portion of the thrust bar (not shown) is received within the cavity of the clamp slide assembly 40 when the clamp slide assembly 40 and the thrust bar are in retracted positions.

The distal transverse portion 46 of the end effector frame 42 includes a proximally facing surface 51 that supports the anvil assembly 44. The proximally facing surface 51 is surrounded by a recess 52 that is defined by a side wall 54 of the distal transverse portion 46 and a shoulder 56 of the distal transverse portion 46. The shoulder 56 includes slots 58. The side wall 54 defines openings 60 that are aligned with the slots 58 and are of a minimal depth, e.g., 0.7 mm, to minimize weakening of the end effector frame.

Figure 7:
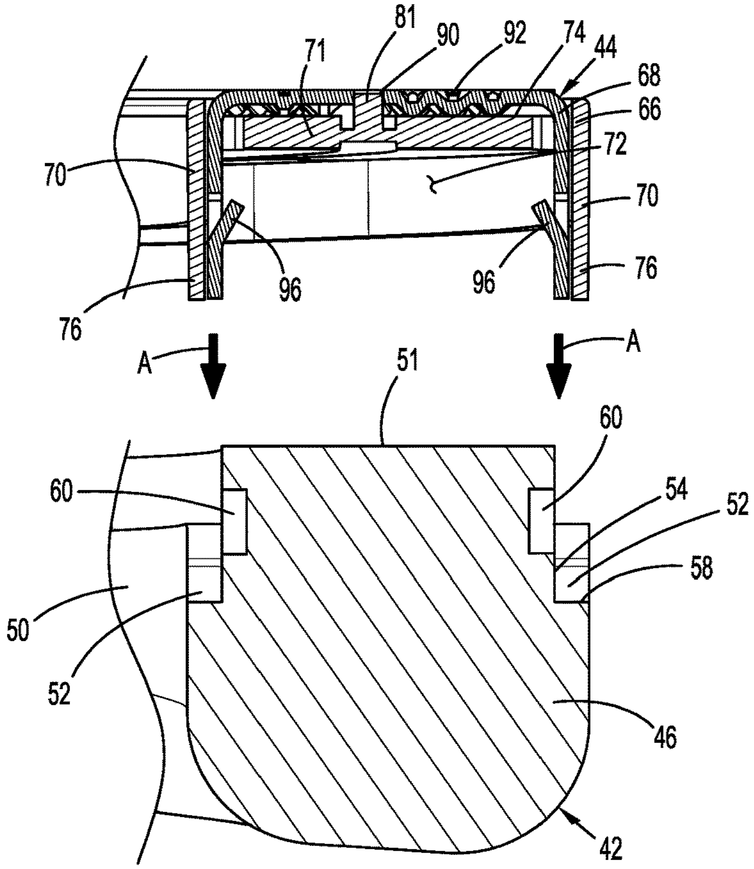
FIG. 7 is a cross-sectional view taken along section line 7-7 of FIG. 6 illustrating the anvil assembly with the anvil assembly spaced from the end effector frame.

The anvil assembly 44 includes a cut plate 66 and an anvil 68. The cut plate 66 includes a base wall 71 (FIG. 6) and a side wall 70 that is positioned about the base wall 71 such that the base wall 71 and the side wall 70 define a proximal recess 72 and a distal recess 74 (FIG. 7). The side wall 70 of the cut plate 66 includes tabs 76 that are received in the slots 58 formed in the side wall 54 of the distal transverse portion 46 of the end effector frame 42. The base wall 71 of the cut plate defines through bores 78 that are aligned with the tabs 76. The base wall 71 also includes a proximally extending rib 81 and guide pin openings 82 and 84 positioned on each end of the rib 80.

The anvil 68 includes a proximal staple forming surface 86 and resilient brackets 88 that extend distally from the staple forming surface 80. The staple forming surface 86 of the anvil 68 defines a knife slot 90 and staple forming depressions 92 that are aligned in rows on each side of the central knife slot 88. In aspects of the disclosure, the staple forming depressions 92 are aligned in three rows on each side of the central knife slot 88. Alternately, the staple forming depressions 92 are aligned in one or more rows on each side of the central knife slot 90 or arranged in a different configuration of staple forming depressions 92. The anvil 68 also defines guide pin openings 94 and 95 that are positioned on opposite ends of the knife slot 90 and are aligned with the guide pin openings 82 and 84 of the cut plate 66.

The resilient brackets 88 include inwardly extending resilient fingers 96 that are aligned with the through bores 78 in the base wall 71 of the cut plate 66 and with the slots 58 formed in the side wall 54 of the distal transverse portion 46 of the end effector frame 42. When the anvil 68 is assembled with the cut plate 66, the anvil 68 is received within the distal recess 74 of the cut plate 66, the brackets 88 of the anvil 68 are received within the through bores 78 of the cut plate 66, and the rib 81 of the cut plate 66 is received within the knife slot 90 of the anvil 68. Each of the resilient fingers 96 in a non-deformed state is bent inwardly at an angle of, e.g., from about 30 degrees to about 60 degrees.

Figure 8:
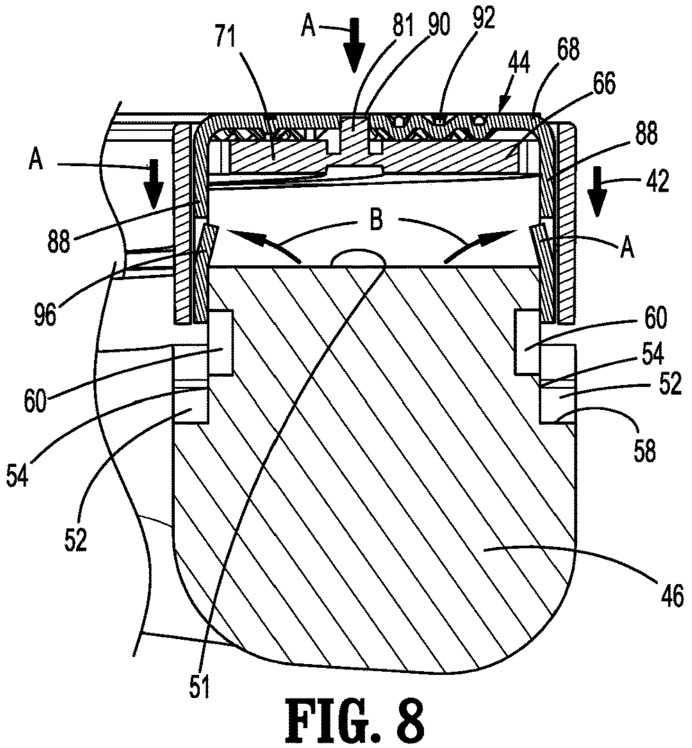
FIG. 8 is a cross-sectional view illustrating the anvil assembly and the end effector frame as the anvil assembly is being attached to the end effector frame.
Figure 9:
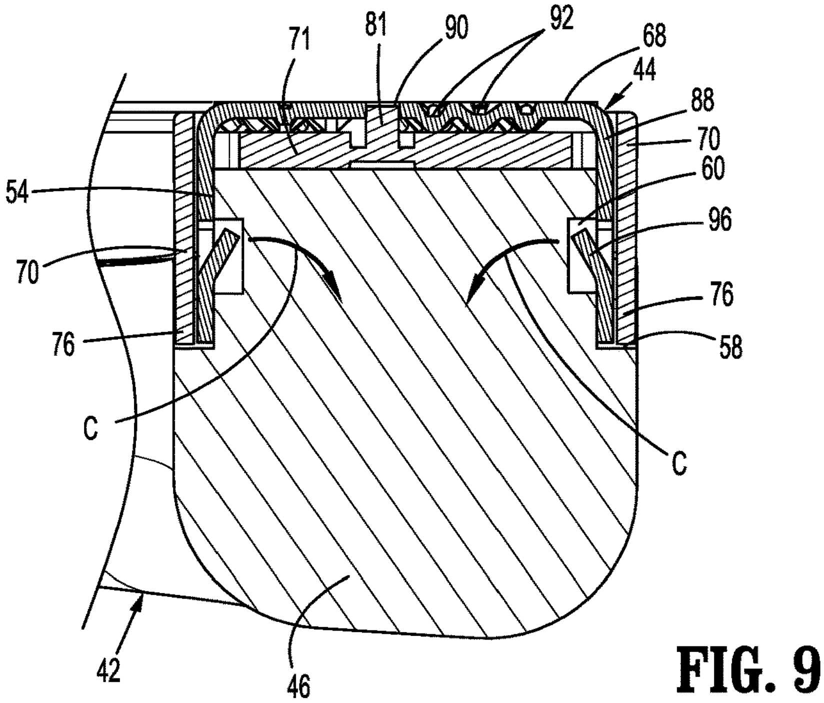
FIG. 9 is a cross-sectional view illustrating the anvil assembly attached to the end effector frame.

FIGS. 7-9 illustrate the anvil assembly 44 as the anvil assembly 44 is secured to the distal transverse portion 46 of the end effector frame 42. To secure the anvil assembly 44 to the distal transverse portion 46 of the end effector frame 42, the tabs 76 on the cut plate 66 are aligned with the slots 58 in the side wall 54 defining the recess 52 of the distal transverse portion 46 of the end effector frame 42 and the anvil assembly 44 is moved in the direction of arrows "A in FIG. 7 to position the proximally facing surface 51 of the transverse portion 46 within the proximal recess 72 of the cut plate 66. As the proximally facing surface 51 of the distal transverse portion 46 is received within the proximal recess 72 of the cut plate 66, the brackets 88 of the anvil 68 move into the recess 52 of the distal transverse portion 46 such that the resilient fingers 96 of the brackets 88 engage the distal transverse portion 46 of the end effector frame 42 and are deformed outwardly in the direction of arrows "B" in FIG. 8. When the fingers 96 move to a position in alignment with the openings 60 in the side wall 54 of the distal transverse portion 46 of the end effector frame 42, the fingers 96 snap back to their deformed configurations in the direction of arrows "C" in FIG. 9 into the openings 60 to secure the anvil assembly 44 to the distal transverse portion 46 of the end effector frame 42 in snap-fit fashion. In this position, the tabs 76 on the cut plate 66 cover the brackets 88 and the snap-fit connection to provide the end effector 16 with a smooth outer surface. When the anvil assembly 44 is secured to the distal transverse portion 46 of the end effector frame 42, the cut plate 66 is sandwiched between the proximally facing surface 51 of the distal transverse portion 46 of the end effector frame 42 and a distal surface of the anvil 68.

Figure 10:
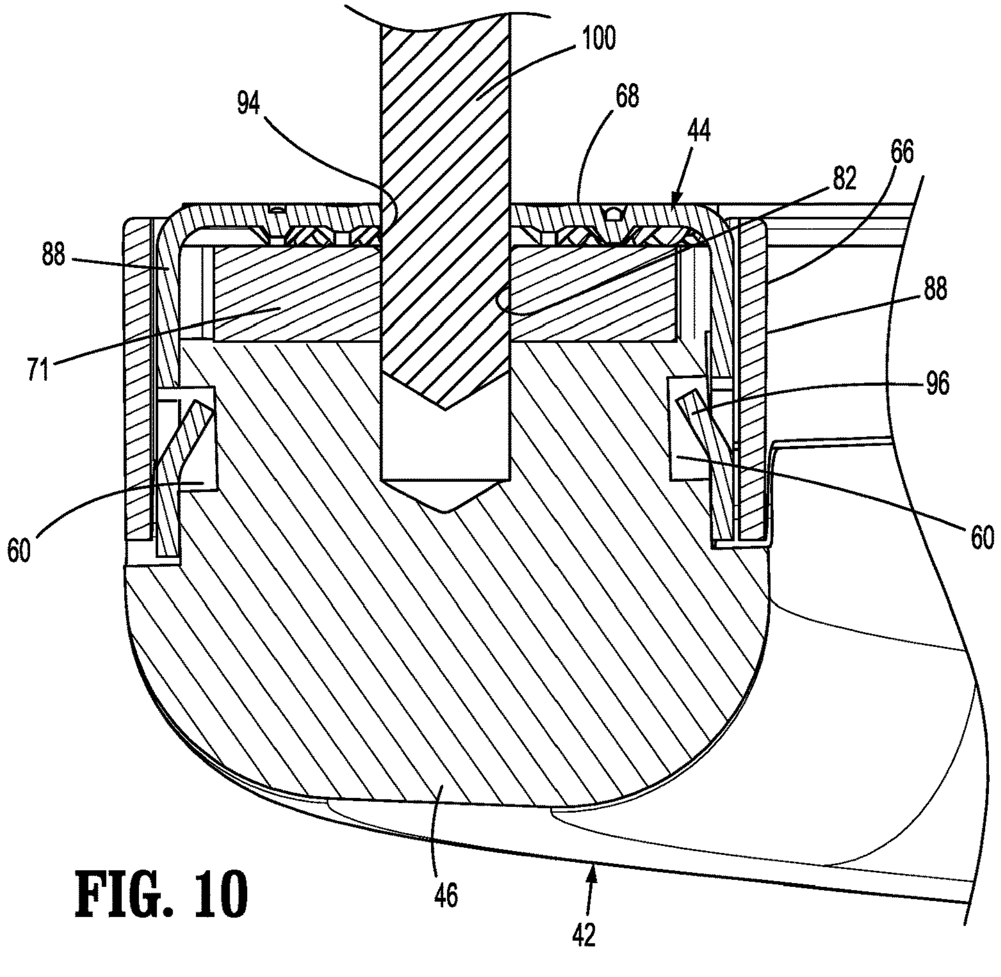
FIG. 10 is a cross-sectional view taken along section line 10-10 of FIG. 1.
Figure 11:
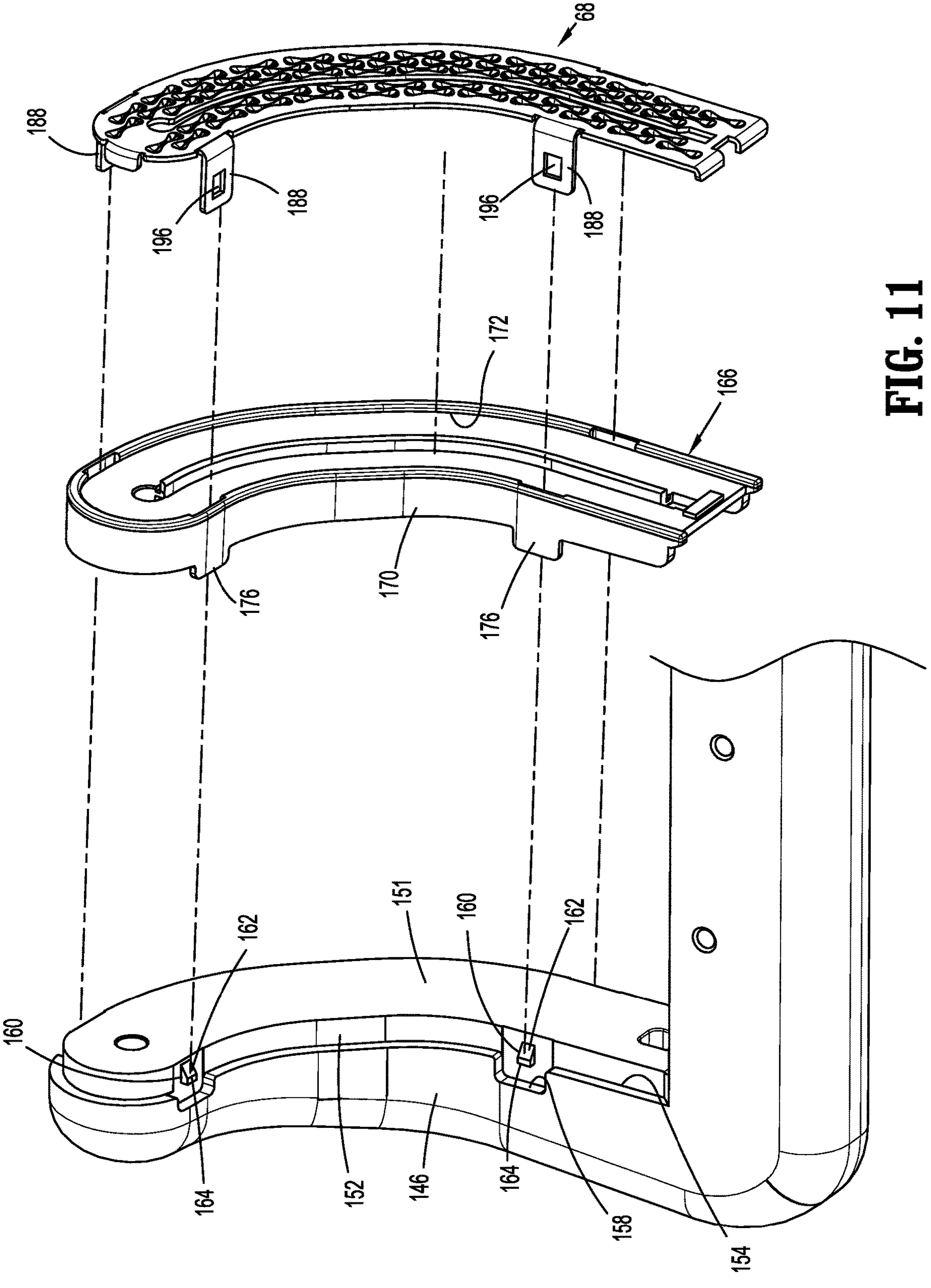
FIG. 11 is a side perspective view of an alternate version of the end effector of the stapling device shown in FIG. 1 illustrating a distal portion of the end effector frame with the anvil assembly separated from the end effector frame.

FIG. 10 illustrates the distal portion of the end effector 16 after a guide pin 100 of the cartridge assembly 38 is advanced through the openings 82 and 94 of the cut plate 66 and the anvil 68. Although not shown, a second guide member (not shown) is also positioned through the openings 84 and 95 of the cut plate 66 and the anvil 68. Receipt of the guide pin 100 within the openings in the anvil assembly 44 aligns the anvil plate 66 on the distal transverse portion 46 of the end effector frame 42 to improve alignment between the cartridge assembly 38 and the anvil assembly 44 when the stapling device 10 (FIG. 1) is moved to the clamped position. More specifically, because the anvil assembly 44 is not rigidly secured to the end effector frame 42, the anvil assembly 44 is able to move slightly or float on the end effector frame 42 such that receipt of the alignment pin or pins 100 within the openings of the anvil assembly 44 can align the anvil assembly 44 with the cartridge assembly 38 (FIG. 1) where slight misalignment exists.

FIGS. 11-15 illustrate an alternate version of the end effector frame and anvil assembly of the stapling device 10 shown generally as end effector frame 142 and anvil assembly 144. The anvil assembly 144 is similar to the anvil assembly 44 described above and includes a cut plate 166 and an anvil 168. The anvil assembly 144 differs from the anvil assembly 44 in that the brackets 188 of the anvil assembly 144 do not include fingers but rather defines openings 196. The cut plate 166 is substantially the same as the cut plate 66 described above and will not be described in further detail herein.

The end effector frame 142 is substantially the same as the end effector frame 42 described above except that the openings 60 in the side wall of the distal transverse portion 46 of the end effector frame 42 are replaced with protrusions 160. In aspects of the disclosure, the protrusions 160 have a tapered proximal face 162 and a flat distal stop surface 164.

Figure 12:
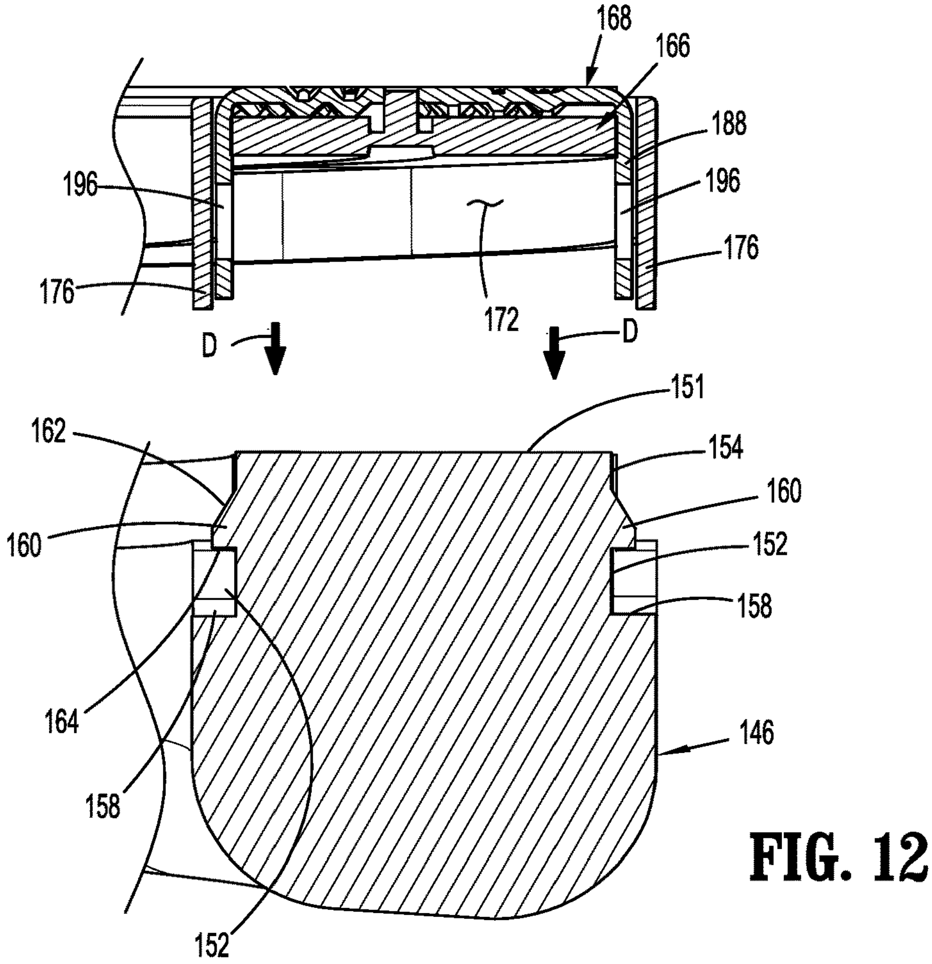
FIG. 12 is a cross-sectional view illustrating the anvil assembly and end effector frame shown in FIG. 11 with the anvil assembly spaced from the end effector frame.
Figure 13:
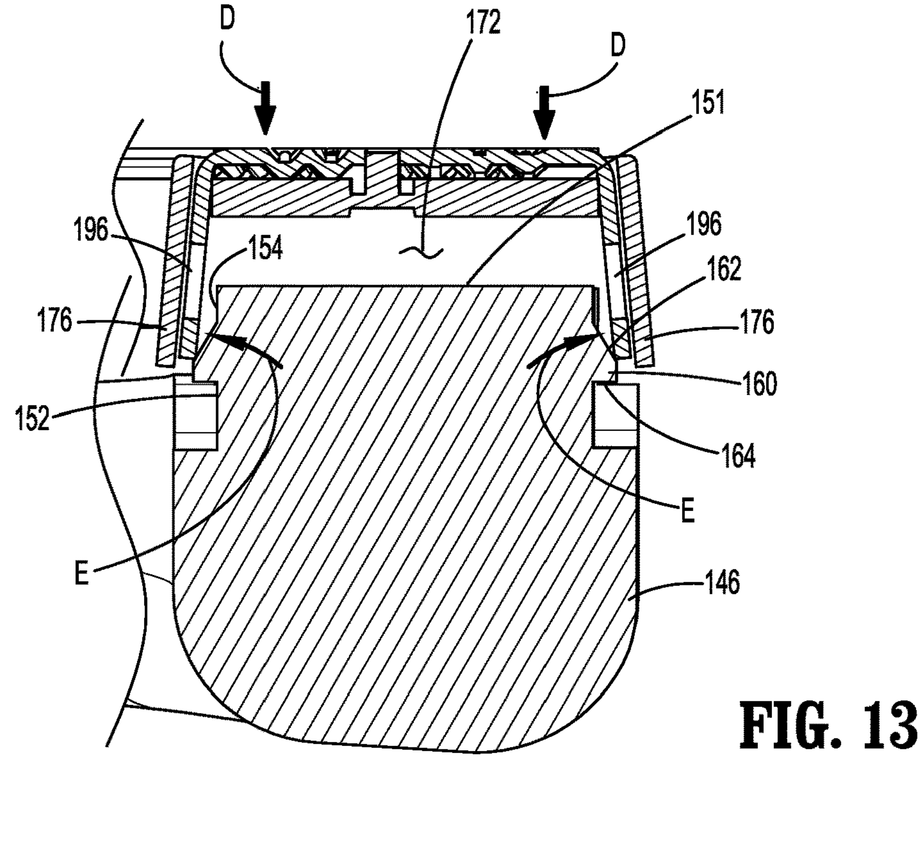
FIG. 13 is a cross-sectional view illustrating the anvil assembly and end effector frame shown in FIG. 12 as the anvil assembly is attached to the end effector frame.
Figure 14:
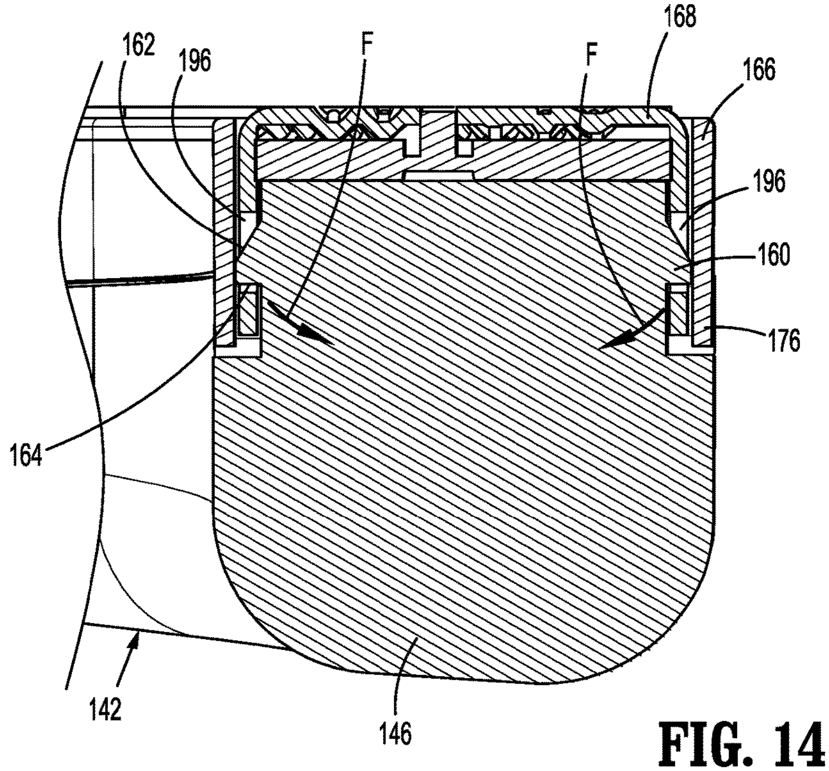
FIG. 14 is a cross-sectional view illustrating the anvil assembly and end effector frame shown in FIG. 13 with the anvil assembly attached to the end effector frame.
Figure 15:
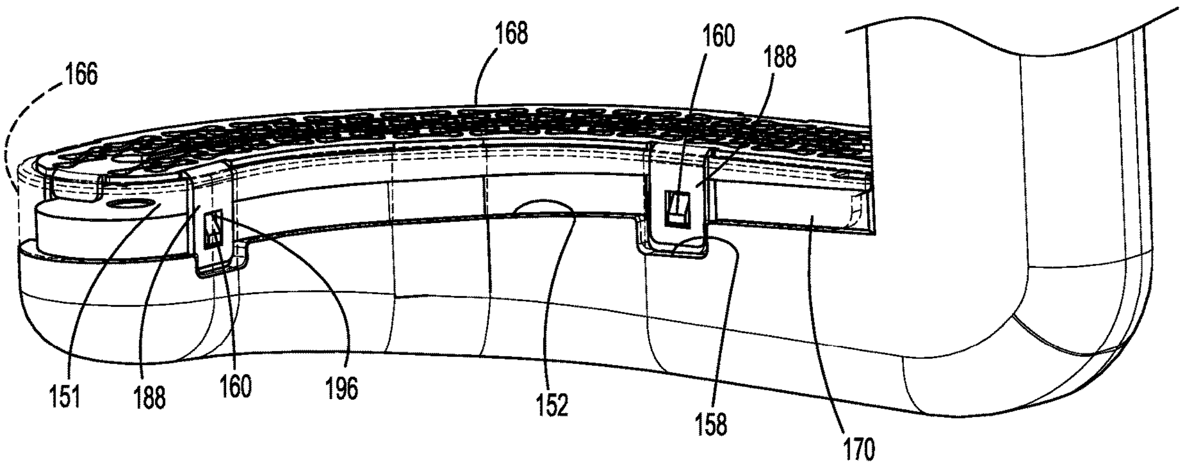
FIG. 15 is a side perspective view of the distal portion of the end effector frame with the anvil assembly attached to the anvil frame.

To secure the anvil assembly 144 to the distal transverse portion 146 of the end effector frame 142, the tabs 176 on the cut plate 166 are aligned with the slots 158 in the side wall 154 defining the recess 152 of the distal transverse portion 146 of the end effector frame 142 and the anvil assembly 144 is moved in the direction of arrows "D" in FIG. 12 to position the proximally facing surface 151 of the transverse portion 146 within the proximal recess 172 of the cut plate 166. As the proximally facing surface 151 of the distal transverse portion 146 is received within the proximal recess 172 of the cut plate 166, the brackets 188 of the anvil 168 move into the recess 152 of the distal transverse portion 146 and engage the tapered proximal face 162 of the protrusions 160 of the distal transverse portion 146 of the end effector frame 42 and are deformed outwardly in the direction of arrows "E" in FIG. 13. When the brackets 188 move to a position in which the openings 196 in the brackets 188 move into alignment with the protrusions 160 on the side wall 154 of the distal transverse portion 146 of the end effector frame 142, the brackets 188 snap back to their deformed configurations in the direction of arrows "F" in FIG. 14 such that the protrusions 160 are received within the openings 196 of the brackets 188 to secure the anvil assembly 144 to the distal transverse portion 146 of the end effector frame 142. When the anvil assembly 144 is secured to the distal transverse portion 146 of the end effector frame 142, the cut plate 166 is sandwiched between the proximally facing surface 151 of the distal transverse portion 146 of the end effector frame 142 and a distal surface of the anvil 168.

The configuration of the anvil assemblies 44, 144 and the end effector frames 42 and 142 simplify the assembly process, reduce cost, and reduce assembly time as compared to a conventional riveting process. In addition, this construction allows the anvil assemblies to float on the end effector frames to facilitate minor corrections of alignment via the guide pin or guide pins.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. An end effector for a surgical device comprising:

an end effector frame including a distal transverse portion, a proximal transverse portion, and a longitudinal portion, the longitudinal portion interconnecting the distal transverse portion and the proximal transverse portion at spaced positions to define a gap between the distal and proximal transverse portions, the distal transverse portion including a proximally facing surface; and an anvil assembly, comprising:

a cut plate including a base wall and a side wall positioned about the base wall, the side wall and the base wall defining a respective proximal recess and a distal recess, the base wall defining through bores, and with the proximally facing surface received within the distal recess; and an anvil received within the proximal recess of the cut plate, the anvil including a staple forming surface and brackets positioned about and extending distally from the staple forming surface, and with the through bores of the cut plate receiving the brackets;

wherein the anvil assembly is secured to the distal transverse portion of the end effector frame via the brackets, in snap-fit fashion, such that the cut plate is sandwiched between the anvil and the proximally facing surface of the distal transverse portion.

2. The end effector of claim 1, wherein the anvil defines a knife slot and the cut plate includes a rib that extends into the knife slot.

3. The end effector of claim 1, wherein each of the brackets includes a resilient finger and the distal transverse portion of the end effector frame defines openings, the resilient fingers received within the openings of the end effector frame in snap-fit fashion to secure the anvil to the distal transverse portion of the end effector frame.

4. The end effector of claim 1, wherein each of the brackets defines an opening and the distal transverse portion of the end effector frame includes a side wall that has protrusions, the protrusions received within the openings of the brackets in snap-fit fashion to secure the anvil to the distal transverse portion of the end effector frame.

5. The end effector of claim 4, wherein the side wall of the distal transverse portion of the end effector frame defines slots and the side wall of the cut plate includes tabs that are received within the slots.

6. The end effector of claim 1, wherein the distal transverse portion of the end effector frame defines a recess that is positioned about the proximally facing surface of the anvil, the side wall of the cut plate received at least partially within the recess.

7. A surgical stapling device comprising:

an elongate frame having a proximal portion and a distal portion and defining a channel;

a clamp slide assembly positioned within the channel, the clamp slide assembly having a distal portion defining a cavity; and an end effector including:

an end effector frame having a distal transverse portion, a proximal transverse portion, and a longitudinal portion, the longitudinal portion interconnecting the distal transverse portion and the proximal transverse portion at spaced positions to define a gap between the distal and proximal transverse portions, the distal transverse portion including a proximally facing surface, the distal portion of the clamp slide assembly received within the gap;

a cartridge assembly supported on the distal portion of the clamp slide assembly within the gap; and an anvil assembly, comprising:

a cut plate including a base wall and a side wall positioned about the base wall, the side wall and the base wall defining a respective proximal recess and a distal recess, and with the proximally facing surface received within the distal recess; and an anvil received within the proximal recess of the cut plate, the anvil including a staple forming surface and brackets positioned about and extending distally from the staple forming surface, and with each of the brackets including a resilient finger received within openings of the distal transverse portion in snap-fit fashion;

wherein the anvil assembly is secured to the distal transverse portion of the end effector frame via the brackets such that the cut plate is sandwiched between the anvil and the proximally facing surface of the distal transverse portion.

8. The surgical stapling device of claim 7, wherein the anvil defines a knife slot and the cut plate includes a rib that extends into the knife slot.

9. The surgical stapling device of claim 7, wherein the distal transverse portion of the end effector frame defines a recess that is positioned about the proximally facing surface of the anvil, the side wall of the cut plate received at least partially within the recess.

10. The surgical stapling device of claim 7, wherein the base wall of the cut plate defines through bores that receive the brackets of the anvil.

11. An end effector comprising:

an end effector frame including a first transverse portion, a second transverse portion, and a longitudinal portion, the longitudinal portion interconnecting the first transverse portion and the second transverse portion at spaced positions to define a gap between the first and second transverse portions, the first transverse portion including a proximally facing surface and a side wall with protrusions extending therefrom;

a cartridge assembly supported within the gap of the end effector frame and movable between an unclamped position spaced from the first transverse portion and a clamped position adjacent the first transverse portion; and an anvil assembly, comprising:

a cut plate including a base wall and a side wall positioned about the base wall, the side wall and the base wall defining a respective proximal recess and a distal recess, and with the proximally facing surface received within the distal recess; and an anvil received within the proximal recess of the cut plate, the anvil including a staple forming surface and brackets positioned about and extending distally from the staple forming surface, and with the brackets defining openings for receiving the protrusions of the first transverse portion in snap-fit fashion;

wherein the anvil assembly is secured to the first transverse portion of the end effector frame via the brackets such that the cut plate is sandwiched between the anvil and the proximally facing surface of the first transverse portion.

* * * * *